United States Patent
Norasak et al.

(10) Patent No.: US 10,512,921 B2
(45) Date of Patent: Dec. 24, 2019

(54) MAINTENANCE APPARATUS FOR VAPORIZING DEVICE

(71) Applicant: FUNAI ELECTRIC CO., LTD., Osaka (JP)

(72) Inventors: Sam Norasak, Lexington, KY (US); Michael A. Marra, III, Lexington, KY (US)

(73) Assignee: FUNAI ELECTRIC CO., LTD. (JP)

(*) Notice: Subject to any disclaimer, the term of this patent is extended or adjusted under 35 U.S.C. 154(b) by 507 days.

(21) Appl. No.: 15/149,664

(22) Filed: May 9, 2016

(65) Prior Publication Data

US 2017/0320087 A1 Nov. 9, 2017

(51) Int. Cl.
- *B05B 1/32* (2006.01)
- *B08B 1/00* (2006.01)
- *F22B 1/28* (2006.01)

(52) U.S. Cl.
CPC .............. *B05B 1/326* (2013.01); *B08B 1/006* (2013.01); *F22B 1/284* (2013.01)

(58) Field of Classification Search
CPC .............. A24F 47/008; A61M 11/042; A61M 15/0026; A61M 15/025; A61M 15/06; A61M 2205/3653; B05B 15/02; B05B 15/50; B05B 1/326; B08B 1/006; B41J 2/16535; F22B 1/284
USPC ......................................... 392/404, 405, 399
See application file for complete search history.

(56) References Cited

U.S. PATENT DOCUMENTS

| | | | | |
|---|---|---|---|---|
| 3,484,023 A | * | 12/1969 | Meshberg | B65D 83/205 222/402.11 |
| 3,584,965 A | * | 6/1971 | Chastanier | A47L 1/08 392/396 |
| 4,853,717 A | * | 8/1989 | Harmon | B41J 2/16523 347/29 |
| 4,911,181 A | | 3/1990 | Vromen et al. | |
| 5,207,785 A | * | 5/1993 | Knickerbocker | B05B 15/52 222/148 |
| 5,249,586 A | * | 10/1993 | Morgan | A24F 47/008 128/200.14 |
| 5,331,953 A | * | 7/1994 | Andersson | A61M 15/00 128/200.14 |
| 5,337,926 A | * | 8/1994 | Drobish | B05B 1/1645 222/309 |
| 5,621,441 A | * | 4/1997 | Waschhauser | B41J 2/16511 347/32 |
| 5,726,421 A | * | 3/1998 | Fleischhauer | A24F 47/008 131/182 |

(Continued)

FOREIGN PATENT DOCUMENTS

| | | | |
|---|---|---|---|
| GB | 2412876 | * | 10/2005 |
| WO | WO9505208 | * | 2/1995 |
| WO | WO2015165105 | * | 11/2015 |

*Primary Examiner* — Ibrahime A Abraham
*Assistant Examiner* — Frederick F Calvetti
(74) *Attorney, Agent, or Firm* — Luedeka Neely Group, PC (57) ABSTRACT

An apparatus for a fluidic ejection device and a fluidic ejection device containing the apparatus. The apparatus includes a pivot member having at least a first position and a second position, a shaft attached on a first end thereof to the pivot member and on a second end distal from the first end to a capping structure, wherein pivot of the pivot member pivots the capping structure from a first capped position to a second uncapped position adjacent an ejection head of the fluidic ejection device.

13 Claims, 10 Drawing Sheets

(56) References Cited

U.S. PATENT DOCUMENTS

| | | | | |
|---|---|---|---|---|
| 5,812,157 A * | 9/1998 | Nguyen | B41J 2/16547 | 347/30 |
| 5,927,558 A * | 7/1999 | Bruce | G01F 11/24 | 222/185.1 |
| 5,946,009 A * | 8/1999 | Youn | B41J 2/16547 | 347/22 |
| 5,954,979 A * | 9/1999 | Counts | A24F 47/008 | 131/194 |
| 6,116,247 A * | 9/2000 | Banyasz | A24F 47/008 | 131/243 |
| 6,125,866 A * | 10/2000 | Nichols | A24F 47/008 | 131/184.1 |
| 6,325,061 B1 * | 12/2001 | Dagsland | A61M 15/00 | 128/203.12 |
| 6,484,717 B1 * | 11/2002 | Dagsland | A61M 15/0065 | 128/203.12 |
| 6,655,380 B1 * | 12/2003 | Andersson | A61M 15/0065 | 128/203.15 |
| 7,275,534 B2 * | 10/2007 | Childers | B05B 15/52 | 128/200.14 |
| 7,779,836 B2 * | 8/2010 | Andersson | A61M 15/0065 | 128/203.15 |
| 8,100,298 B2 * | 1/2012 | Marquardt | B65D 83/206 | 222/153.11 |
| 8,127,968 B2 * | 3/2012 | Yerby | B65D 83/206 | 222/153.11 |
| 8,128,194 B2 * | 3/2012 | Okada | B41J 2/16547 | 347/29 |
| 8,327,847 B2 * | 12/2012 | Scarrott | A61M 15/009 | 116/307 |
| 9,861,136 B2 | 1/2018 | Li et al. | | |
| 2002/0109744 A1 * | 8/2002 | Shindo | B41J 2/1433 | 347/23 |
| 2004/0135842 A1 * | 7/2004 | Saksa | B41J 2/16505 | 347/33 |
| 2004/0150690 A1 * | 8/2004 | Childers | B05B 15/52 | 347/22 |
| 2007/0267031 A1 | 11/2007 | Hon | | |
| 2009/0283094 A1 * | 11/2009 | Hamano | A61M 15/02 | 128/203.15 |
| 2013/0192615 A1 * | 8/2013 | Tucker | H01C 17/00 | 131/328 |
| 2013/0298905 A1 | 11/2013 | Levin et al. | | |
| 2014/0137862 A1 * | 5/2014 | Chen | A61M 15/0065 | 128/203.15 |
| 2014/0190997 A1 * | 7/2014 | Presley | A46B 11/00 | 222/390 |
| 2014/0345634 A1 | 11/2014 | Zuber et al. | | |
| 2015/0053202 A1 * | 2/2015 | Knell | A61M 15/0096 | 128/200.23 |
| 2015/0053203 A1 * | 2/2015 | Knell | A61M 15/0093 | 128/200.23 |
| 2016/0143354 A1 * | 5/2016 | Liu | A24F 47/008 | 131/329 |
| 2016/0198770 A1 * | 7/2016 | Alarcon | A24F 47/008 | 392/404 |
| 2016/0219934 A1 * | 8/2016 | Li | A24F 47/008 | |
| 2017/0354807 A1 * | 12/2017 | Lozevski | B05B 15/63 | |
| 2018/0256834 A1 * | 9/2018 | Hepworth | A24F 47/002 | |

\* cited by examiner

MAINTENANCE APPARATUS FOR VAPORIZING DEVICE

TECHNICAL FIELD

The disclosure is directed to fluidic structures and the maintenance apparatus for fluidic ejection devices.

BACKGROUND AND SUMMARY

One of the applications of fluidic structures is to jet a solution on to another device where a secondary function may be performed. A common secondary function is to vaporize a solution using a heater such that the contents of the solution can be vaporized so as to deliver the solution as a gaseous substance. Applications of such technology include, but are not limited to, metering and vaporizing device for electronic cigarettes, vapor therapy, gaseous pharmaceutical delivery, vapor phase reactions for microlabs, and the like. In all of these applications, a fluidic ejection head is used to eject fluid onto a heated surface for vaporization of the fluid into a discharge conduit. For some applications, the fluids to be ejected have relatively low vaporization temperatures and thus can evaporate over time through ejection nozzles in the ejection head. For other applications, contamination of the ejection head between uses may be a problem. In some applications, the fluids may leave a residue on the ejection head that will, over time, inhibit the proper ejection of fluid from the ejection head or that may plug the ejection nozzles. Maintaining such devices so that precise fluid ejection is obtained is a problem due to the small size of such devices. Conventional maintenance devices for fluidic ejection heads require a relatively large area for capping and cleaning the ejection heads.

Accordingly, what is needed is an apparatus that can be operated to protect the ejection head when the device is not in use and can be used to clean the ejection head in order to maintain proper ejection of fluid.

In view of the foregoing, embodiments of the disclosure provide an apparatus for a fluidic ejection device and a fluidic ejection device containing the apparatus. The apparatus includes a pivot member having at least a first position and a second position, a shaft attached on a first end thereof to the pivot member and on a second end distal from the first end to a capping structure, wherein pivot of the pivot member pivots the capping structure from a first capped position to a second uncapped position adjacent an ejection head of the fluidic ejection device.

In one embodiment there is provided a fluidic ejection device that includes a fluidic ejection head in fluid flow communication with a fluid reservoir, a heater for vaporizing fluid ejected from the fluidic ejection head, an exit conduit in flow communication from the heater, an ejection head capping structure disposed between the heater and the fluidic ejection head, and a selection device operatively connected to the ejection head capping structure for moving the capping structure from a first capped position to a second uncapped position adjacent the fluidic ejection head.

In another embodiment, the capping structure includes a nozzle cap for capping the ejection head when the pivot member is pivoted to the first capped position.

In other embodiments, the capping structure includes an aperture therein for fluid flow therethrough when the pivot member is pivoted to the second uncapped position and a wiper blade for cleaning the ejection head when the pivot member is pivoted to the first capped position and to the second uncapped position.

In some embodiments, the pivot member is disposed on a vapor exit conduit of the fluidic ejection device. In other embodiments, the capping structure is moved between the first and second positions by a selection device operatively connected to the ejection head capping structure.

BRIEF DESCRIPTION OF THE DRAWINGS

Other features and advantages of the inventive may be evident by reference to the following detailed description, drawings and claims wherein:

DETAILED DESCRIPTION OF EMBODIMENTS

Figure 1:
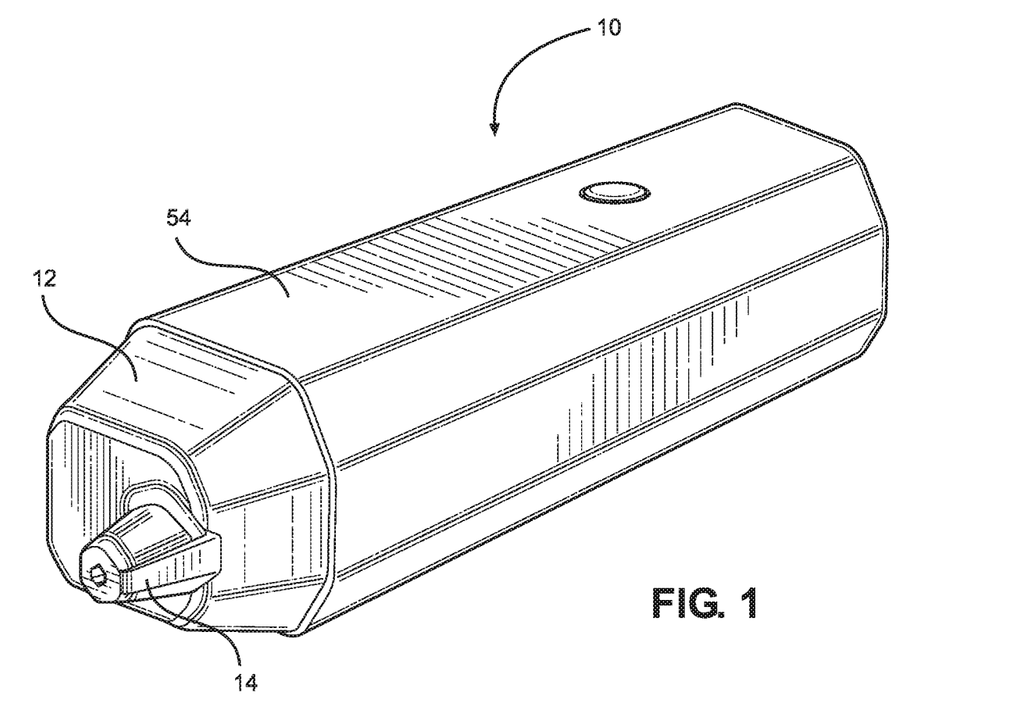
FIG. 1 is a perspective view of a fluidic ejection device according to an embodiment of the disclosure.
Figure 2A:
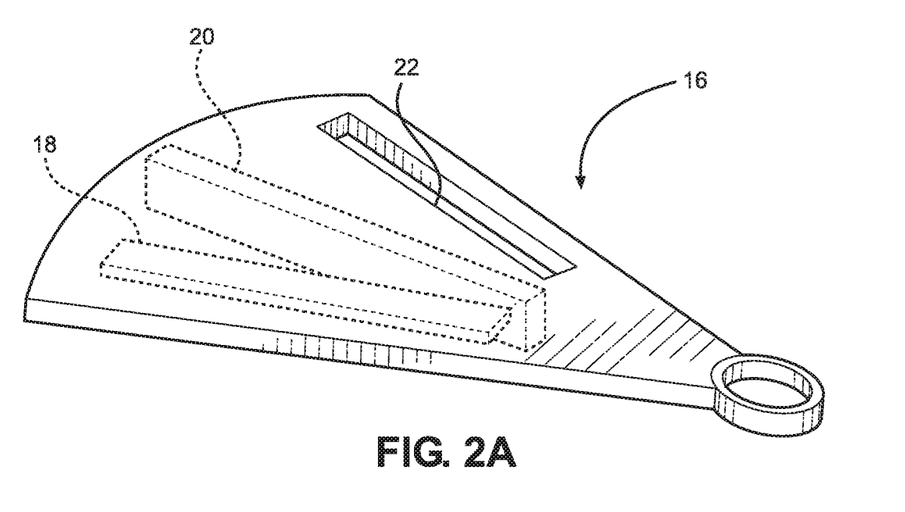
FIG. 2A is a top perspective view, not to scale, of a capping structure for a fluidic ejection head according to a first embodiment of the disclosure.
Figure 2B:
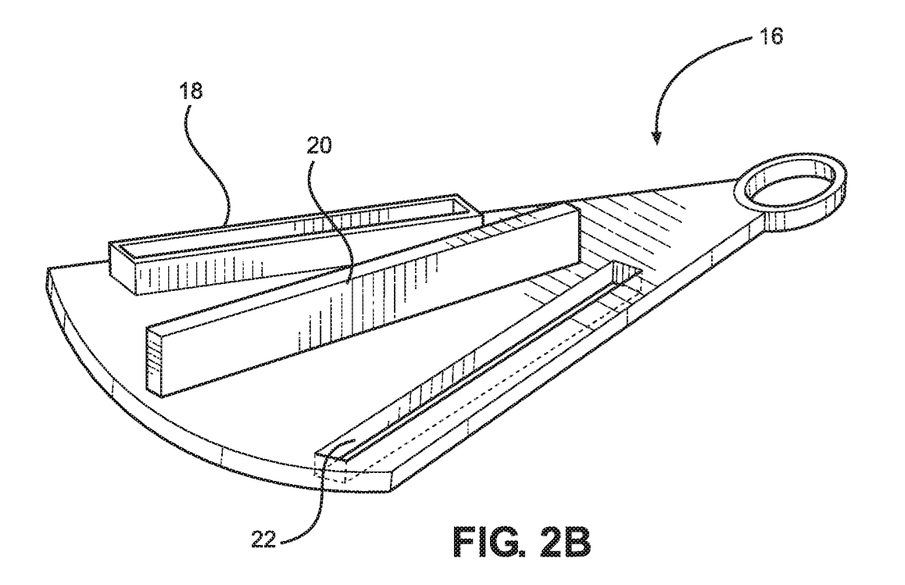
FIG. 2B is a bottom perspective view, not to scale, of a capping structure for a fluidic ejection head according to a first embodiment of the disclosure.

The disclosure is directed to fluidic ejection and vaporizing devices 10 as shown generally in FIG. 1. Such devices 10 may be used for a wide variety of applications wherein a liquid is ejected onto a vaporizing heater to provide a vapor stream as described in more detail below. Such devices 10 are typically hand held devices such as electronic cigarettes that have a mouth piece 12 for inhaling vapors generated by the device 10. The mouthpiece 12 may include a vapor exit conduit 14 for flow of vapors out of the device 10. The liquid to be vaporized is typically contained with the body of the device 10 or in a separately removable cartridge. A fluidic ejection head is provided in fluid flow communication with the liquid container and provides a preselected amount of liquid to the vaporizing heater. As described above, it may be necessary to prevent excess evaporation from the fluidic ejection head and/or prevent contamination of the ejection head when the ejection head is not in use. However, the small size of the fluidic ejection device makes it difficult to use any kind of conventional capping mechanism for the ejection head.

Figure 3:
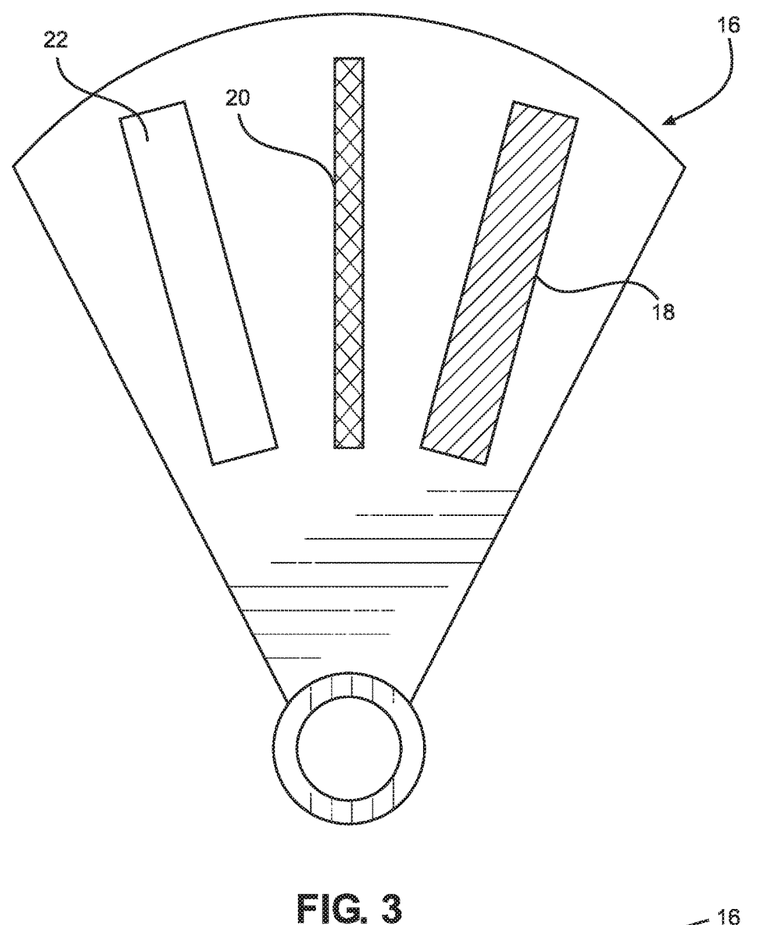
FIG. 3 is a plan bottom view, not to scale, of the capping structure of FIG. 2.
Figure 4:
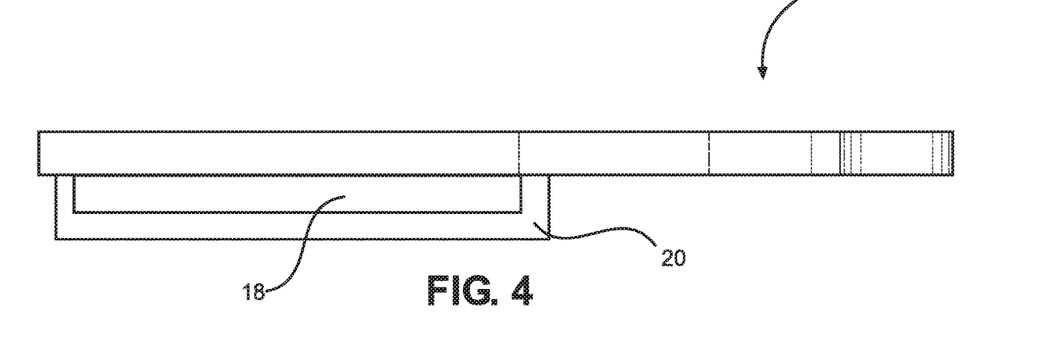
FIG. 4 is an elevational view not to scale, of the capping structure of FIG. 2.

With reference to FIGS. 2-5, there is provided a capping structure 16 that may be used to provide capping and cleaning functions to a fluidic ejection head for the fluidic ejection device 10 described above. In one embodiment, FIGS. 2A and 2B show perspective views of the capping structure 16, FIG. 3 shows a bottom plan view of the capping structure 16 and FIG. 4 shows an elevational view of the capping structure 16. The capping structure 16 has a triangular-shape and includes an ejection head cap 18, a wiper blade 20, and an aperture 22. The capping structure 16 is configured to be pivoted over the ejection head to provide a capping function, a cleaning function and an uncapped function. As shown in FIG. 4, the ejection head cap 18 and the wiper blade 20 are configured to come in contact with the ejection head. During pivot of the capping structure 16 from a first capping position to a second uncapped position, the wiper blade 20 sweeps across the ejection head to remove debris and contaminants from the ejection head.

Figure 5:
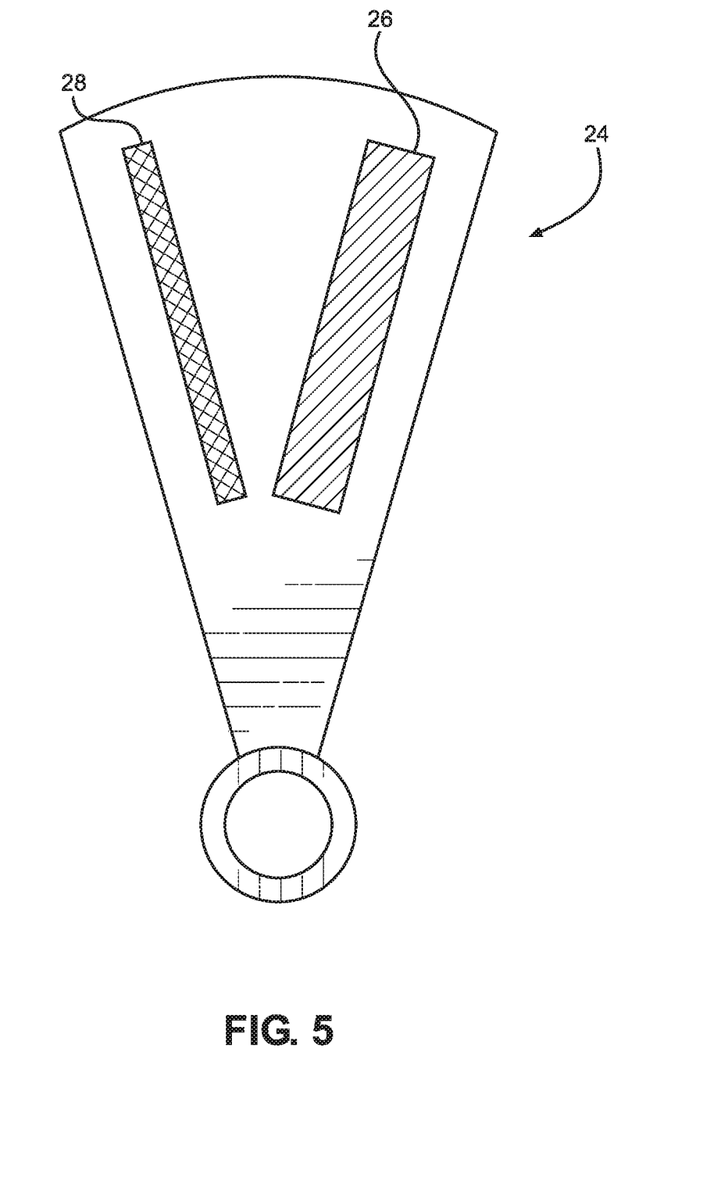
FIG. 5 is a plan bottom view, not to scale, of an alternative capping structure according to the disclosure.

In an alternative embodiment shown in FIG. 5, the capping structure 24 is configured to contain only an ejection head cap 26 and a wiper blade 28. Accordingly, pivot of the capping structure 24 from a capped position to an uncapped position provides the same capping and cleaning functions as the capping structure 16, but requires a smaller structure 24 that can be moved past ejection nozzles of a fluidic ejection head without interfering with fluid ejection from the fluidic ejection head.

Figure 6:
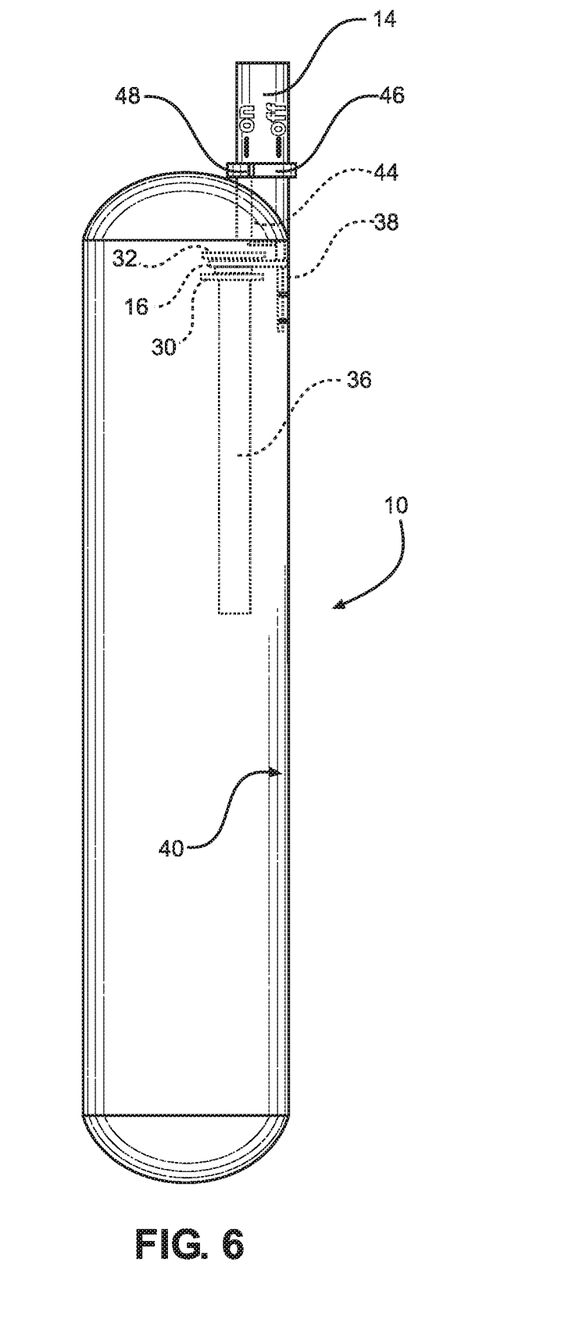
FIG. 6 is an elevational view, not to scale, of a fluidic ejection device according to one embodiment of the disclosure.
Figure 7:
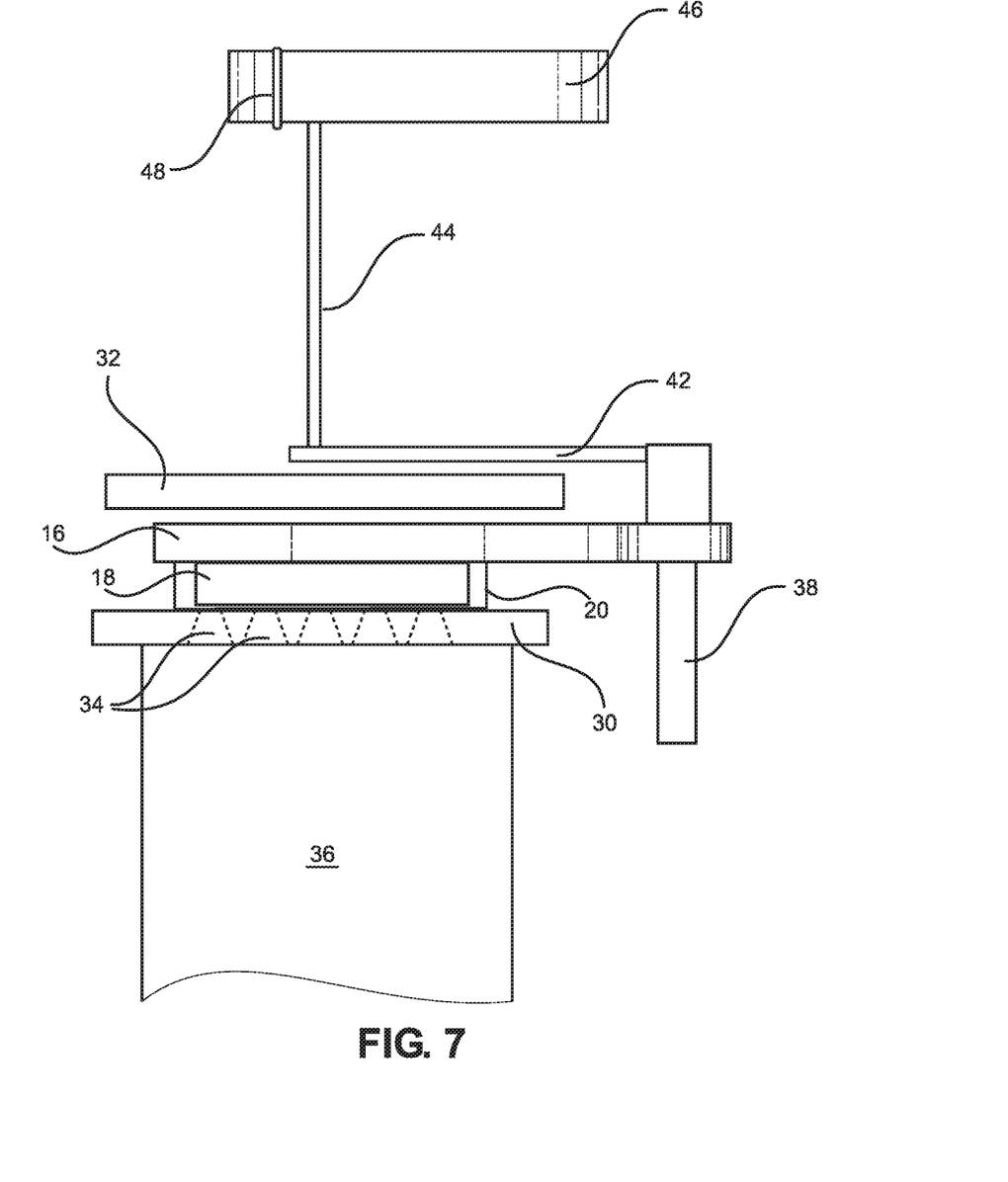
FIG. 7 is a partial elevational view, not to scale, of an ejection head and capping structure for the fluidic ejection device of FIG. 6.
Figure 8:
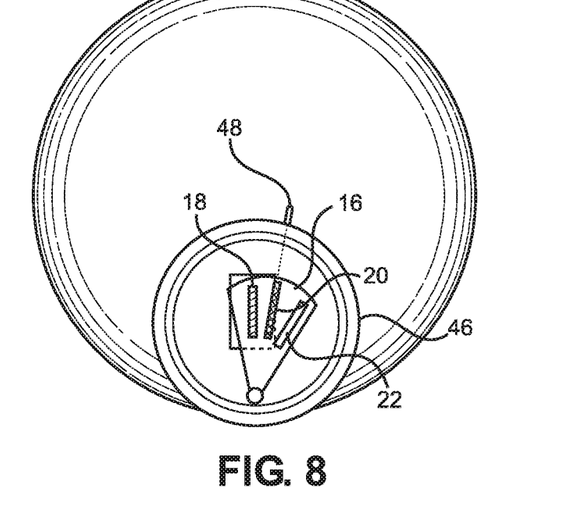
FIG. 8 is top plan view, not to scale, through an exit conduit of a fluidic ejection device showing a capping structure in a first capping position.
Figure 9:
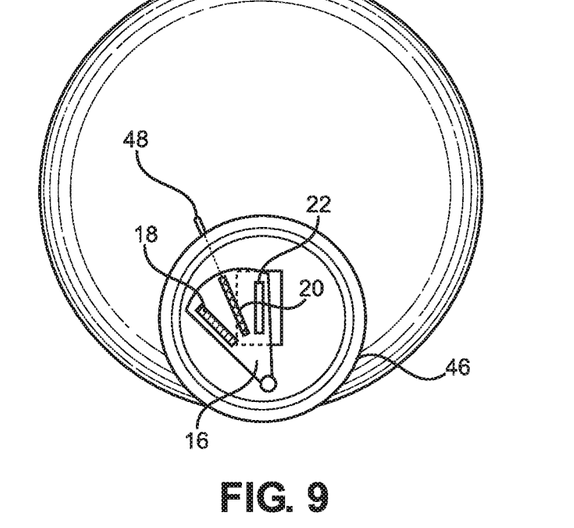
FIG. 9 is top plan view, not to scale, through an exit conduit of a fluidic ejection device showing a capping structure in a second uncapped position.

With reference to FIGS. 6 and 7, there is shown a fluidic ejection device 10 that includes the capping structure 16 and a mechanism for moving the capping structure 6 from a capped position to an uncapped position. As shown, in FIGS. 6 and 7, the capping structure 16 is disposed in the fluidic ejection device 10 between a fluidic ejection head 30 and a vaporizing heater 32. In the capped position, the ejection head cap 18 is disposed over ejection nozzles 34 of the ejection head 30 to prevent evaporation and ejection of fluid from a fluid reservoir 36 attached to the ejection head 30. The capping structure 16 is attached by means of a shaft 38 and linkages 42 and 44 to a pivot member 46 for pivoting the capping structure over the ejection head 30 to cap, clean and uncap the ejection head as shown in FIGS. 8-9. The shaft 38 may be rotatably attached to an inner wall 40 of the fluidic ejection device 10. In the first position shown in FIG. 8, the capping structure 16 is in the capped position which is signified as an "off" position. In the off position, fluid is prevented from escaping from the ejection head 30 and thus no vapor is generated by the fluidic ejection device 10. FIG. 9 shows the capping structure 16 in a second uncapped position, signified as the "on" position, wherein aperture 22 is disposed over the ejection head nozzles 34 so that fluid can be ejected onto the vaporizing heater 32. When moving the capping structure 16 from the off to on positions or from the on to off positions, the wiper blade 20 is caused to sweep across the ejection head 30 to remove debris and contaminants from the ejection head 30.

As shown in FIG. 6, the capping structure 16, ejection head 30 and vaporizing heater 32 are positioned in the fluidic ejection device 10 so that vapors generated by the vaporizing heater 32 may be exhausted through a vapor exit conduit 14 of the mouth piece 12 (FIG. 1) of the fluidic ejection device. Accordingly, as shown in FIG. 6, the pivot member 46 is disposed on the vapor exit conduit 14 for manually moving the capping structure 16 between the capped and uncapped positions. The pivot member 46 may include an indicator 48 to show if the ejection head is capped or uncapped (off or on). Accordingly, a user may easily determine if the fluidic ejection device 10 is in condition for use.

In the embodiment shown in FIGS. 6-9, the entire mechanism for capping and uncapping the ejection head 30 is disposed in and adjacent to the vapor exit conduit 14. Accordingly, there is no special sealing arrangement needed to prevent vaporized fluids from escaping from the fluidic ejection device 10.

Figure 10:
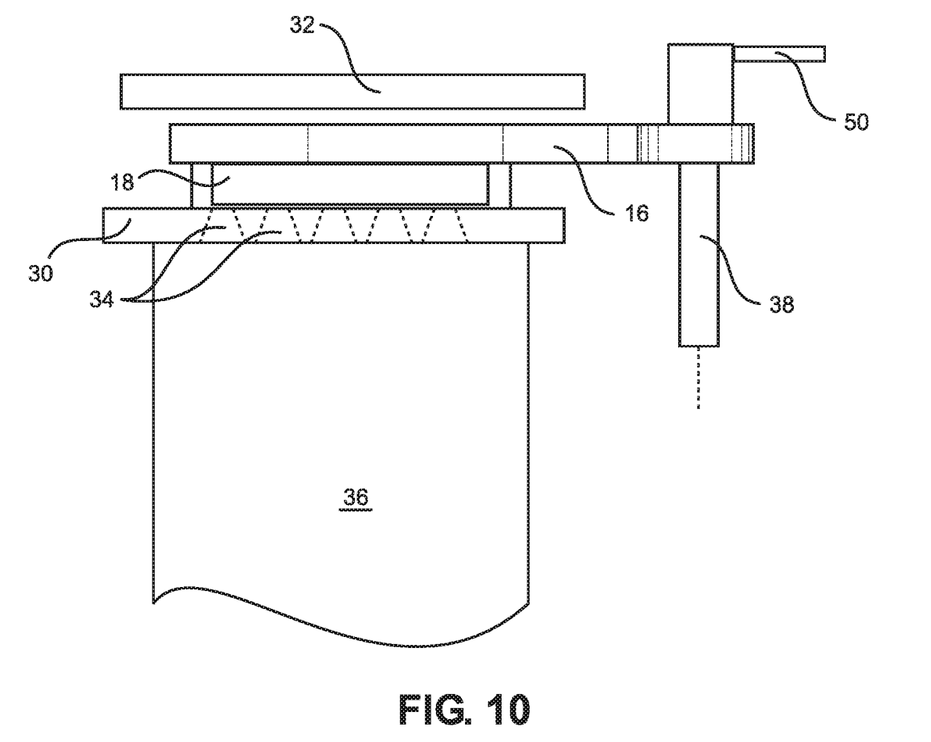
FIG. 10 is a partial elevational view, not to scale, of a capping structure for a fluidic ejection device according to another embodiment of the disclosure.
Figure 11:
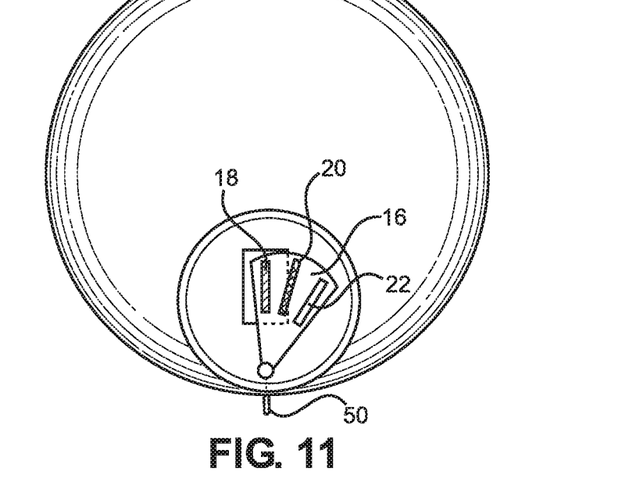
FIG. 11 is top plan view, not to scale, through an exit conduit of a fluidic ejection device showing the capping structure of FIG. 10 in a first capping position for the fluidic ejection device.
Figure 12:
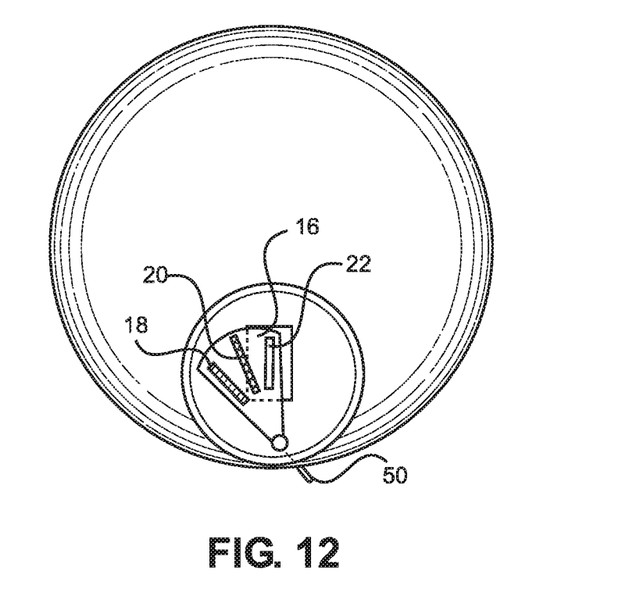
FIG. 12 is top plan view, not to scale, through an exit conduit of a fluidic ejection device showing the capping structure of FIG. 10 in a second uncapped position for the fluidic ejection device.
Figure 13:
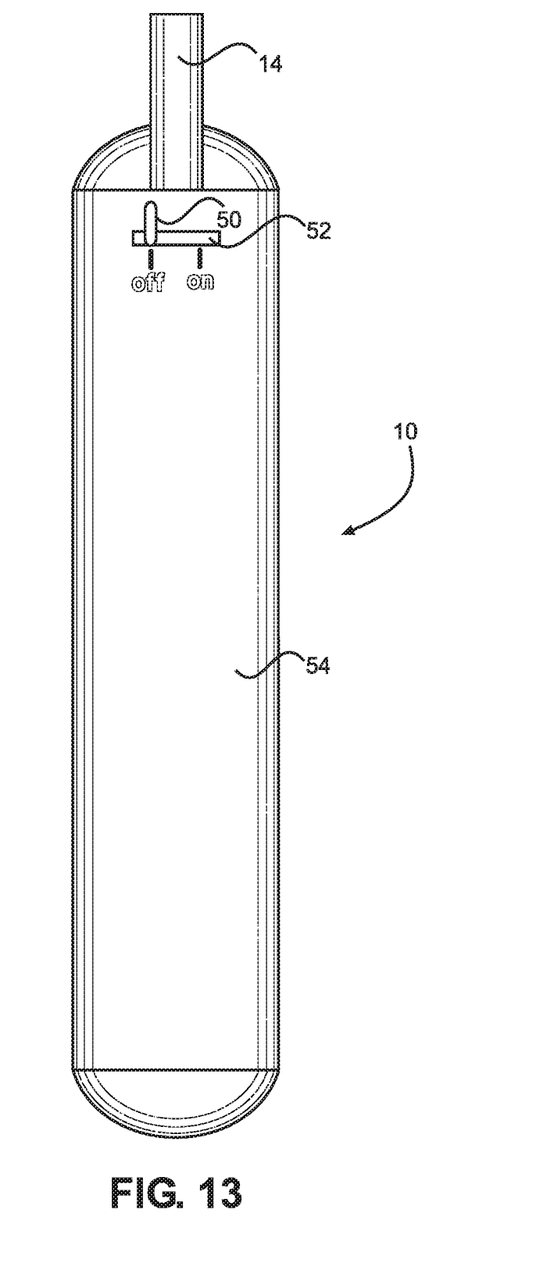
FIG. 13, is an elevational view, not to scale, of a fluidic ejection device according to the embodiment of FIG. 10.

In another embodiment, illustrated in FIGS. 10-12, a slide lever 50 is used to position the capping structure 16 with respect to the ejection head 30. The slide lever 50 is attached by means of shaft 38 to the capping structure 16 for moving the capping structure 16 between the first capped position to the second uncapped position as shown in FIGS. 11 and 12. In this embodiment in FIG. 13, the slide lever 50 is disposed through a slot 52 in the body 54 of the fluidic ejection device. The slot 52 may include a sealing flap (not shown) to prevent vapors from escaping from the slot when the capping structure is in the "on" position.

The capping structure 16, as well as the body 54 of the fluidic ejection device may be made from a wide variety of materials including plastics, metals, glass, ceramic and the like provided the materials are compatible with the fluids to be ejected and vaporized by the device 10. A particularly suitable material may be selected from polyvinyl chloride, high density polyethylene, polycarbonate, stainless steel, surgical steel, and the like. All parts, including the mouthpiece 12, vapor exit conduit 14, and body 54 that come in contact with fluids and vapors may be made of plastic. The wiper blade 20 may be made of a resilient material such as an elastomeric material, natural rubber, fluoropolymer, and the like for wiping the ejection head 30. As with the other components of the fluidic ejection device the wiper blade 20 should be made of a material that is resistant to the fluids used in and vapors generated by the fluidic ejection device 10.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. An apparatus for a fluidic ejection head of a fluidic ejection device comprising a triangular plate having a pivot point on an apex end thereof for rotation of the plate between at least a first position and a second position, a shaft attached on a first end thereof to the plate at the apex end of the plate, a shaft movement ring or slide lever attached to the shaft adjacent to a second end thereof, and an ejection head cap having four interconnected walls attached to and extending from a planar surface of the plate, wherein the ejection head cap is movable from a first capped position adjacent to the ejection head of the fluidic ejection device and to a second uncapped position with respect to the ejection head of the fluidic ejection device, and wherein the triangular plate is disposed between the ejection head and a vaporizing heater in the fluidic ejection device.

2. The apparatus of claim 1, wherein the triangular plate includes an aperture therein for fluid flow therethrough when the plate is moved to the second uncapped position.

3. The apparatus of claim 1, wherein the triangular plate further comprises a rectangular prism shaped wiper blade for cleaning the ejection head when the plate is moved between the first capped position and to the second uncapped position wherein the wiper blade is attached to and extends outwardly from the planar surface of plate.

4. The apparatus of claim 1, wherein the shaft movement ring or slide lever is disposed on a vapor exit conduit of the fluidic ejection device.

5. The apparatus of claim 4, wherein the slide lever is movable from a first position to a second position on the vapor exit conduit in order to rotate the shaft.

6. The apparatus of claim 4, wherein the shaft movement ring is rotated about the vapor exit conduit from a first position to a second position in order to rotate the shaft.

7. The apparatus of claim 1, wherein the triangular plate is disposed adjacent a vapor exit conduit of the fluidic ejection device.

8. A fluidic ejection device comprising a fluidic ejection head in fluid flow communication with a fluid reservoir, a heater for vaporizing fluid ejected from the fluidic ejection head, an exit conduit in flow communication from the heater, an ejection head cap having four interconnected walls attached to and extending from a planar surface of a triangular plate disposed between the heater and the fluidic ejection head, and a shaft movement ring or slide lever operatively connected to the triangular plate for moving the ejection head cap from a first capped position to a second uncapped position adjacent the fluidic ejection head.

9. The fluidic ejection device of claim 8, wherein triangular plate includes an aperture therein for fluid flow therethrough to the vaporizing heater when the ejection head cap is moved to the second uncapped position from the first capped position.

10. The fluidic ejection device of claim 9, wherein the triangular plate further comprises a rectangular prism shaped wiper blade for cleaning the ejection head when the ejection head cap is moved between the first capped position and the second uncapped position, wherein the wiper blade is attached to and extends outwardly from the planar surface of plate.

11. The fluidic ejection device of claim 9, wherein the shaft movement ring or slide lever is disposed on the exit conduit of the fluidic ejection device.

12. The fluidic ejection device of claim 11, wherein the shaft movement ring or slide lever is attached to a first end of a shaft disposed in the exit conduit, wherein a second end of the shaft is attached to the triangular plate for movement thereof.

13. The fluidic ejection device of 11, wherein the shaft movement ring is rotated about the exit conduit to rotate a shaft and move the ejection head cap on triangular plate between the first capped position and the second uncapped position.

* * * * *